(12) United States Patent
Akkaraju

(10) Patent No.: US 12,372,644 B2
(45) Date of Patent: *Jul. 29, 2025

(54) THUMB-DOMINANT ULTRASOUND IMAGING SYSTEM

(71) Applicant: Exo Imaging, Inc., Santa Clara, CA (US)

(72) Inventor: Sandeep Akkaraju, Wellesley, MA (US)

(73) Assignee: Exo Imaging, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/520,636

(22) Filed: Nov. 28, 2023

(65) Prior Publication Data

US 2024/0094386 A1 Mar. 21, 2024

Related U.S. Application Data

(63) Continuation of application No. 16/978,139, filed as application No. PCT/US2019/020338 on Mar. 1, 2019, now Pat. No. 11,828,844.

(Continued)

(51) Int. Cl.
*G01S 15/58* (2006.01)
*A61B 8/00* (2006.01)
*G01S 7/52* (2006.01)

(52) U.S. Cl.
CPC ........ *G01S 15/586* (2013.01); *G01S 7/52053* (2013.01); *G01S 7/52079* (2013.01); *A61B 8/4254* (2013.01); *A61B 8/4427* (2013.01)

(58) Field of Classification Search
None
See application file for complete search history.

(56) References Cited

U.S. PATENT DOCUMENTS

2004/0138569 A1 7/2004 Grunwald et al.
2007/0078340 A1 4/2007 Wilcox
(Continued)

FOREIGN PATENT DOCUMENTS

CN 103202712 A 7/2013
CN 106293328 A 1/2017
(Continued)

OTHER PUBLICATIONS

PCT/US2019/020338 International Search Report and Written Opinion dated Jun. 18, 2019.

*Primary Examiner* — Jeffrey G Hoekstra
*Assistant Examiner* — Nyrobi Celestine
(74) *Attorney, Agent, or Firm* — Morgan, Lewis & Bockius LLP

(57) ABSTRACT

A portable ultrasound imaging system for thumb-dominant operations can use a portable ultrasound probe that is configured to be operable using a first hand of the user. The system can use a mobile device that has a mobile application installed thereon. The mobile application can have a user interface and be configured to be operable using a second hand of the user. The system can permit direct electronic communication between the portable ultrasound probe and the mobile device and allow a user to control an operation of the portable ultrasound probe for imaging via user interaction with the user interface.

21 Claims, 16 Drawing Sheets

Related U.S. Application Data

(60) Provisional application No. 62/638,471, filed on Mar. 5, 2018.

(56) References Cited

U.S. PATENT DOCUMENTS

| | | |
|---|---|---|
| 2010/0022882 A1 | 1/2010 | Duckworth |
| 2010/0145195 A1 | 6/2010 | Hyun |
| 2010/0148030 A1 | 6/2010 | Lin |
| 2011/0055447 A1 | 3/2011 | Costa |
| 2013/0215079 A1 | 8/2013 | Johnson et al. |
| 2014/0059486 A1* | 2/2014 | Sasaki ............... A61B 8/0866 715/810 |
| 2015/0065881 A1 | 3/2015 | Cho |
| 2015/0238168 A1 | 8/2015 | Poland |
| 2015/0245816 A1 | 9/2015 | Poland |
| 2015/0297185 A1 | 10/2015 | Mander et al. |
| 2015/0324070 A1 | 11/2015 | Kim |
| 2016/0015368 A1 | 1/2016 | Poland |
| 2016/0041674 A1* | 2/2016 | Xia ............... G06F 3/04817 345/173 |
| 2016/0113724 A1 | 4/2016 | Stolka |
| 2016/0179326 A1 | 6/2016 | Aswathanaravana |
| 2016/0378286 A1* | 12/2016 | Ke ............... G06F 3/04886 715/764 |
| 2017/0095230 A1 | 4/2017 | Richard et al. |
| 2017/0095231 A1 | 4/2017 | Richard et al. |
| 2017/0103732 A1 | 4/2017 | Schantz |
| 2017/0300205 A1* | 10/2017 | Villa ............... G06F 3/04842 |
| 2017/0360405 A1 | 12/2017 | Rothberg et al. |
| 2018/0055483 A1 | 3/2018 | Hunter |
| 2018/0188946 A1* | 7/2018 | Jun ............... G16H 40/63 |
| 2019/0038260 A1 | 2/2019 | Lee |
| 2019/0269386 A1 | 9/2019 | Raju |
| 2020/0015876 A1 | 1/2020 | Chou |

FOREIGN PATENT DOCUMENTS

| | | |
|---|---|---|
| JP | 2003299652 A | 10/2003 |
| JP | 2006521613 A | 9/2006 |
| JP | 2009163278 A | 7/2009 |
| JP | 2009543615 A | 12/2009 |
| KR | 20160138787 A | 12/2016 |
| KR | 20170093632 A | 8/2017 |
| WO | WO-2009149499 A1 | 12/2009 |
| WO | WO-2010148030 A2 | 12/2010 |
| WO | WO-2015185976 A1 | 12/2015 |

* cited by examiner

THUMB-DOMINANT ULTRASOUND IMAGING SYSTEM

CROSS-REFERENCE TO RELATED APPLICATIONS

This application is a continuation of U.S. patent application Ser. No. 16/978,139, filed Sep. 3, 2020, which is a U.S. National Phase of International Application No. PCT/US2019/020338, filed Mar. 1, 2019, which is an international application claiming the benefit of and priority to U.S. Provisional Application No. 62/638,471, filed Mar. 5, 2018, each of which is hereby incorporated by reference in its entirety.

BACKGROUND OF THE INVENTION

During ultrasound imaging, an ultrasound probe is typically held in the dominant hand of the user relegating the user to utilize his/her second hand for a mobile device or other devices for controlling imaging operations.

SUMMARY OF THE INVENTION

Existing ultrasound systems include an imaging probe that is commonly held with a dominant hand of an operator, thereby presenting a significant hurdle for simultaneously usage of a mobile device by the same operator.

There is an urgent and unmet need for portable ultrasound devices that can be used in the field in conjunction with a mobile device for acquiring ultrasound images. In order to effectively reduce the difficulties of using an ultrasound imaging application on a mobile device to acquire images, a single-handed user interface is needed. In some cases, a user interface that is designed mainly with the thumb is preferred as it allows the user to focus on positioning the ultrasound probe for the best quality images as opposed to fidgeting with the user interface.

Disclosed herein are portable ultrasound systems. Such systems can include a user interface for interacting with an ultrasound imager (also known as ultrasound probe or simply probe) on a mobile device. The user interface in the present disclosure is designed for single-handed operation and takes advantage of a thumb-dominant interface. Disclosed herein, a thumb-dominant interface is configured to allow a user to use the thumb to interact with a lot of features, icons, and other accessories at the user interface thus enabling user operation of the mobile application with no or minimal need to use other fingers. In some embodiments, a thumb-dominant interface is advantageous as it enables the user to hold the mobile phone and operate the mobile application with the same hand. While the interface is designed primarily for the thumb, the user at his/her convenience can use other finger(s) to interact with the interface. Further, the interface herein advantageously enables novice users to use ultrasound imaging systems herein and find clinically valid views of organs/tissue by providing features such as displaying orientation or attitude of the ultrasound probe as an overlay on the image and automatically providing guidance instructions on how to move the probe displayed as overlay.

In one aspect, disclosed herein, is a portable ultrasound imaging system for thumb-dominant operations comprising: a portable ultrasound probe, wherein the portable ultrasound probe is configured to be operable using a first hand of the user; a mobile device comprising a mobile application installed thereon, the mobile application comprising a user interface, the mobile application configured to be operable using a second hand of the user while the user operates the portable ultrasound probe with the first hand; and direct electronic communication between the portable ultrasound probe and the mobile device, the direct electronic communication configured to allow a user to control an operation of the portable ultrasound probe for imaging via user interaction with the user interface. In some embodiments, the portable ultrasound probe is configured to be operable using only the first hand of the user. In some embodiments, the first hand is a dominant hand or a non-dominant hand of the user. In some embodiments, the mobile application or the user interface is configured to be operable using only the second hand of the user. In some embodiments, the mobile application or the user interface is configured to be operable using only one finger of the second hand of the user. In some embodiments, the second hand is a dominant hand or a non-dominant hand of the user. In some embodiments, the mobile device comprises an input device, the input device configured to allow user interaction with the user interface of the mobile application. In some embodiments, the input device is a touch screen. In some embodiments, the user interaction with the user interface via the input device comprises: a swipe, a tap, a press, a press and hold, a drag, a scrub, a scroll, a pinch, a zoom, a circling, a contouring, a crossing, or a combination thereof. In some embodiments, the user interface comprises a single finger accessibility zone. In some embodiments, the user interface comprises access to one or more commonly used commands or functions within the single finger accessibility zone for controlling operations of the portable ultrasound probe. In some embodiments, the user interface comprises access to one or more non-commonly used commands or functions outside of the single finger accessibility zone for controlling operations of the portable ultrasound probe. In some embodiments, the single finger accessibility zone is scaled based on the size of the user's hand, size of the mobile device, size of the input device, display size of the mobile application, display size of the user interface, or a combination thereof. In some embodiments, the single finger accessibility zone comprises an image display region and a control region. In some embodiments, the access comprises text, symbols, icons, or a combination thereof displayed within or outside of the image display region. In some embodiments, the control region comprises an imaging toolbar, an imaging mode selector, an imaging preset button, an access to image processing, or a combination thereof. In some embodiments, the text, symbols, icons, or a combination thereof are at least partly overlaid with an image, after the user activate the access via an input device. In some embodiments, the portable ultrasound probe comprises a communication interface that is configured to allow the direct electronic communication between the portable ultrasound probe and the mobile device. In some embodiments, the mobile device comprises a second communication interface that is configured to allow the direct electronic communication between the portable ultrasound probe and the mobile device. In some embodiments, the direct electronic communication between the portable ultrasound probe and the mobile device is wired or wireless. In various embodiments, the portable ultrasound probe comprises an ultrasound transducer, an IMU sensor, a pressure sensor, a force sensor, a haptic feedback actuator, a speaker, a light source, a microphone, a unit for probe control, or any combination thereof. In some embodiments, the portable ultrasound probe and/or mobile device are configured to provide haptic feedback with regard to operating conditions, for example, by varying the intensity of feedback until the user attains optimal orientation. Suitable forms of haptic feedback include vibration, force, and/or motion. In some embodiments, the portable ultrasound probe and/or mobile device are configured to provide audio signals regarding operating conditions, for example, by warning the user of the probe head temperature via a verbal warning or beeping as the temperature approaches the maximum allowable operating temperature. In some embodiments, the portable ultrasound probe and/or mobile device are configured to provide visual signals regarding operating conditions, for example, by changing an LED color and/or intensity or other visual indicator on the probe and/or mobile device in response to the user attaining optimal orientation. In some embodiments, the portable ultrasound imaging system for thumb-dominant operation comprises features allowing a user to add patient information, notes, annotations, and other text measurements to an ultrasound examination in simple manners. For example, pre-configured text for various cardiac image views (4-chamber, 2-chamber, etc.) in dropdown menus can be selected rather than the user manually typing this information using the mobile device keyboard interface. In another embodiment the user can record voice annotations as digitized audio clips using a microphone on the mobile device, which can be placed at specific points in the image ("dropping a pin on an image"). In another embodiment the voice annotations can be transcribed into human readable text and appended to the image exam. In such embodiments, the thumb dominant UI is enhanced by voice annotation and/or pre-populated texts by reducing or simplifying the manual typing a typical user would do on a conventional system.

In another aspect, disclosed herein is a computer-implemented system comprising: a mobile device comprising: at least one processor, an operating system configured to perform executable instructions, a memory, and a computer program including instructions executable by the mobile device to create a mobile application configured to be operable using a single hand of a user, the mobile application comprising: a direct electronic communication to a portable ultrasound probe; and a user interface allowing a user to select one or more commands or functions thereby controlling operations of the portable ultrasound probe via the direct electronic communication; wherein the user interface comprises a single finger accessibility zone that is scaled based on size of the user's hand, size of the mobile device, size of the input device, display size of the mobile application, display size of the user interface, or a combination thereof. In some embodiments, the one or more commands or functions comprises: using one or more preset imaging parameters for imaging a specific tissue or organ of a patient; selecting an imaging mode; selecting an equalizer setting; acquiring an image or a video; accessing a previously acquired image or video; accessing an image post-processing application; setting a focal point; adjusting ultrasonic pressure level, brightness level of an image, or contrast of an image; activating a Doppler overlay; displaying user instruction for moving the portable ultrasound probe; changing a magnification of an image displayed at the mobile device or an image to be acquired; or a combination thereof. In some embodiments, the portable ultrasound probe and/or mobile device are configured to provide haptic feedback with regard to operating conditions, for example, by varying the intensity of feedback until the user attains optimal orientation. Suitable forms of haptic feedback include vibration, force, and/or motion. In some embodiments, the portable ultrasound probe and/or mobile device are configured to provide audio signals regarding operating conditions, for example, by warning the user of the probe head temperature via a verbal warning or beeping as the temperature approaches the maximum allowable operating temperature. In some embodiments, the portable ultrasound probe and/or mobile device are configured to provide visual signals regarding operating conditions, for example, by changing an LED color and/or intensity or other visual indicator on the probe and/or mobile device in response to the user attaining optimal orientation.

BRIEF DESCRIPTION OF THE DRAWINGS

A better understanding of the features and advantages of the present subject matter will be obtained by reference to the following detailed description that sets forth illustrative embodiments and the accompanying drawings of which.

DETAILED DESCRIPTION OF THE INVENTION

Figure 1A:
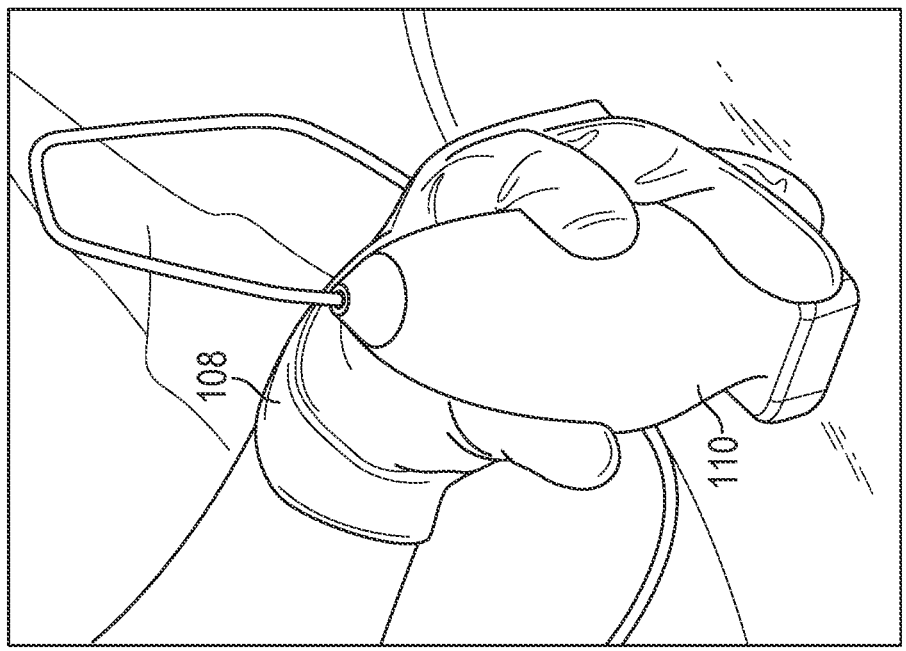
FIG. 1A shows an exemplary system disclosed herein which is configured for two-handed operation where in the probe is held in one hand and the mobile device is held in the other hand of the user.
Figure 1A:
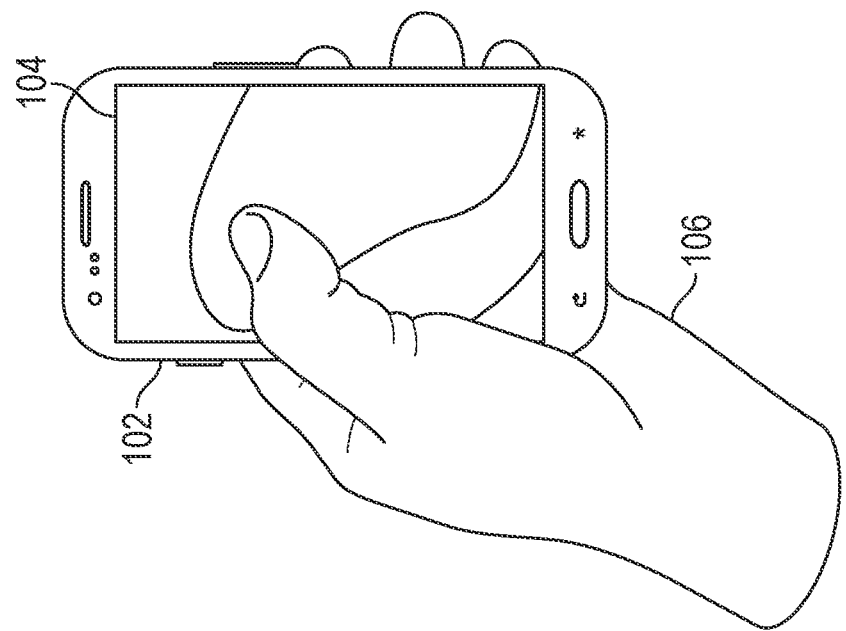

Existing ultrasound systems include an imaging probe that is commonly held with a dominant hand of an operator, thereby presenting a significant hurdle for simultaneously usage of a mobile device by the same operator.

There is an urgent and unmet need for portable ultrasound devices that can be used in the field in conjunction with a mobile device for acquiring ultrasound images. In order to effectively reduce the difficulties of using an ultrasound imaging application on a mobile device to acquire images, a single-handed user interface is needed. In some cases, a user interface that is designed mainly with the thumb is preferred as it allows the user to focus on positioning the ultrasound probe for the best quality images as opposed to fidgeting with the user interface.

Disclosed herein are portable ultrasound systems. Such system can include a user interface for interacting with an ultrasound imager (also known as ultrasound probe or simply probe) on a mobile device. The user interface in the present disclosure is designed for single-handed operation and takes advantage of a thumb-dominant interface. While the interface is designed primarily for the thumb, the user at his/her convenience can use other finger(s) to interact with the interface.

Disclosed herein, in some embodiments, is a portable ultrasound imaging system for thumb-dominant operations comprising: a portable ultrasound probe, wherein the portable ultrasound probe is configured to be operable using a first hand of the user; a mobile device comprising a mobile application installed thereon, the mobile application comprising a user interface, the mobile application configured to be operable using a second hand of the user while the user operates the portable ultrasound probe with the first hand; and direct electronic communication between the portable ultrasound probe and the mobile device, the direct electronic communication configured to allow a user to control an operation of the portable ultrasound probe for imaging via user interaction with the user interface. In some embodiments, the portable ultrasound probe is configured to be operable using only the first hand of the user. In some embodiments, the first hand is a dominant hand or a non-dominant hand of the user. In some embodiments, the mobile application or the user interface is configured to be operable using only the second hand of the user. In some embodiments, the mobile application or the user interface is configured to be operable using only one finger of the second hand of the user. In some embodiments, the second hand is a dominant hand or a non-dominant hand of the user. In some embodiments, the mobile device comprises an input device, the input device configured to allow user interaction with the user interface of the mobile application. In some embodiments, input device is a touch screen. In some embodiments, the user interaction with the user interface via the input device comprises: a swipe, a tap, a press, a press and hold, a drag, a scrub, a scroll, a pinch, a zoom, a circling, a contouring, a crossing, or a combination thereof. In some embodiments, the user interface comprises a single finger accessibility zone. In some embodiments, the user interface comprises access to one or more commonly used commands or functions within the single finger accessibility zone for controlling operations of the portable ultrasound probe. In some embodiments, the user interface comprises access to one or more non-commonly used commands or functions outside of the single finger accessibility zone for controlling operations of the portable ultrasound probe. In some embodiments, the single finger accessibility zone is scaled based on size of the user's hand, size of the mobile device, size of the input device, display size of the mobile application, display size of the user interface, or a combination thereof. In some embodiments, the single finger accessibility zone comprises an image display region and a control region. In some embodiments, the access comprises text, symbols, icons, or a combination thereof displayed within or outside of the image display region. In some embodiments, the control region comprises an imaging toolbar, an imaging mode selector, an imaging preset button, an access to image processing, or a combination thereof. In some embodiments, the text, symbols, icons, or a combination thereof are at least partly overlaid with an image, after the user activate the access via an input device. In some embodiments, the portable ultrasound probe comprises a communication interface that is configured to allow the direct electronic communication between the portable ultrasound probe and the mobile device. In some embodiments, the mobile device comprises a second communication interface that is configured to allow the direct electronic communication between the portable ultrasound probe and the mobile device. In some embodiments, the direct electronic communication between the portable ultrasound probe and the mobile device is wired or wireless. In some embodiments, the portable ultrasound probe comprises an ultrasound transducer, an IMU sensor, a pressure sensor, a force sensor, a unit for probe control, or a combination thereof.

Disclosed herein, in some embodiments, is a computer-implemented system comprising: a mobile device comprising: at least one processor, an operating system configured to perform executable instructions, a memory, and a computer program including instructions executable by the mobile device to create a mobile application configured to be operable using a single hand of a user, the mobile application comprising: a direct electronic communication to a portable ultrasound probe; and a user interface allowing a user to select one or more commands or functions thereby controlling operations of the portable ultrasound probe via the direct electronic communication; wherein the user interface comprises a single finger accessibility zone that is scaled based on size of the user's hand, size of the mobile device, size of the input device, display size of the user interface, or a combination thereof. In some embodiments, the one or more commands or functions comprises: using one or more preset imaging parameters for imaging a specific tissue or organ of a patient; selecting an imaging mode; selecting an equalizer setting; acquiring an image or a video; accessing a previously acquired image or video; accessing an image post-processing application; setting a focal point; adjusting ultrasonic pressure level, brightness level of an image, or contrast of an image; activating a Doppler overlay; displaying user instruction for moving the portable ultrasound probe; changing a magnification of an image displayed at the mobile device or an image to be acquired; or a combination thereof.

Disclosed herein, in some embodiments, is a computer-implemented system comprising: a mobile device comprising: at least one processor, an operating system configured to perform executable instructions, a memory, and a computer program including instructions executable by the mobile device to create a mobile application configured to be operable using a single hand of a user, the mobile application comprising: a direct electronic communication to a portable ultrasound probe; and a user interface allowing a user to select one or more commands or functions thereby controlling operations of the portable ultrasound probe via the direct electronic communication, wherein the one or more commands or functions comprises: displaying guidance instruction to the user for moving the portable ultrasound probe; and displaying real-time orientation of the portable ultrasound probe.

Certain Definitions

Unless otherwise defined, all technical terms used herein have the same meaning as commonly understood by one of ordinary skill in the art to which this invention belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by about 10%, 5%, or 1%, including increments therein.

Overview

Disclosed herein, in some embodiments, is a portable ultrasound imaging system that is designed to enable ultrasound imaging utilizing a thumb (or other dominant finger) dominant user interface of a mobile application installed on a mobile device.

FIG. 1A shows an exemplary embodiment of the portable ultrasound imaging system disclosed herein. In this particular embodiment, the probe 110 is held in the right hand 108 and the mobile device 102 is held in the left hand 106. In some embodiments, the user selects to operate the probe 110 with a non-dominant hand or dominant hand, and the mobile application/user interface 104 with the other hand. In some embodiments, the single-handed user interface may be reconfigured for left-handed and right-handed people.

Portable Probe

Disclosed herein is a portable probe for ultrasound imaging. An exemplary embodiment of the portable probe 110 is shown in FIG. 1A. In some embodiments, the probe is sized, shaped, or of a weight that allows its proper operation using a single hand of the user. In some embodiments, the probe is wirelessly communicating with other devices to optimize its portability and accessibility using a single hand. In some embodiments, the probe has a maximal length, width, diameter, height, or thickness in the range of about 3 cm to about 15 cm. In some embodiments, the probe has a maximal weight of less than 5, 4, 3, 2, 1, or 0.5 pound, including increments therein.

Figure 1B:
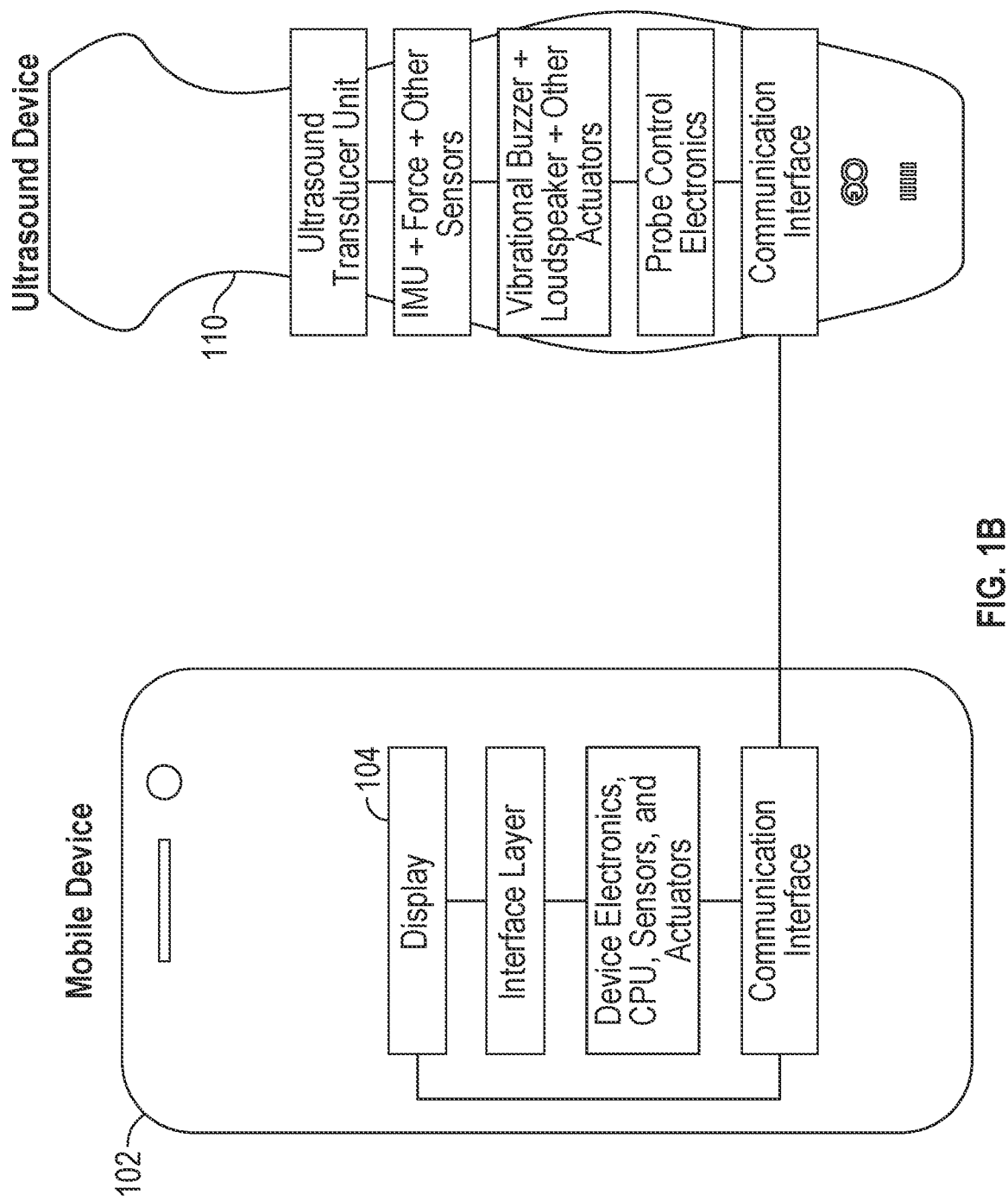
FIG. 1B shows schematic diagrams of the ultrasound probe and the mobile device; in this case, there are direct communications between the mobile device and ultrasound probe.

As shown in FIG. 1B (right), the probe 110 includes an ultrasonic transducer, one or more sensors, one or more haptic actuators, one or more speakers, one or more light sources (e.g., LEDs), electronics for controlling probe operation (e.g., frequency of ultrasound waves), a communications interface, or equivalent herein, a communications element, a rechargeable power source, or a combination thereof.

In some embodiments, the one or more sensors include an inertial sensor (e.g., accelerometers, gyroscopes, inertial measurement units (IMUs)), a pressure sensor, a force sensor, or any other type of sensors.

In some embodiments, the portable probe includes a digital display. In some embodiments, the portable probe does not include a digital display to effectively reduce its size and weight.

In some embodiments, the portable probe includes user feedback components including, by way of non-limiting examples, haptic feedback components, audio feedback components, and visual feedback components, including combinations thereof. In further embodiments, a haptic feedback component comprises a vibration, force, and/or motion actuator, such as a vibrational buzzer. In further embodiments, an audio feedback component comprises a speaker, such as a piezoelectric speaker. In further embodiments, a visual feedback component comprises a light source, such as a dimmable and/or color changing LED.

In some embodiments, the portable probe includes components allowing a user to record voice annotation. In further embodiments, components allowing a user to record voice annotation comprise a microphone. In still further embodiments, a microphone is coupled with a user interface element for activating/deactivating the microphone and/or recording features. In other embodiments, a microphone is always active and listens for a trigger to start and/or stop recording features.

In some embodiments, the portable probe includes components allowing a user to select one or more texts from a list of pre-populated texts. In some embodiments, a list of pre-populated texts is presented on a display and the user selects one or more via touch, voice, or the like. In various embodiments, a voice annotation and/or user-selected text pertains to a patient, a procedure, an image, a region of an image, a property of an image, review of one or more images, billing issues, or attestation through digital signatures, etc.

Mobile Device and Mobile Application

In some embodiments, described herein include a mobile device, or use of the same. In further embodiments, the mobile device includes one or more hardware central processing units (CPUs) or general-purpose graphics processing units (GPGPUs) that carry out the device's functions. In still further embodiments, the mobile device further comprises an operating system configured to perform executable instructions. In some embodiments, the mobile device is optionally connected to a computer network. In further embodiments, the mobile device is optionally connected to the Internet such that it accesses the World Wide Web. In still further embodiments, the mobile device is optionally connected to a cloud computing infrastructure. In other embodiments, the mobile device is optionally connected to an intranet. In other embodiments, the mobile device is optionally connected to a data storage device.

In accordance with the description herein, suitable mobile devices include, by way of non-limiting examples, mobile smartphones, tablet computers, and personal digital assistants. Those of skill in the art will recognize that many smartphones are suitable for use in the system described herein. Suitable tablet computers include those with booklet, slate, and convertible configurations, known to those of skill in the art.

In some embodiments, the mobile device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, Chrome® OS, and Palm® WebOS®.

In some embodiments, the mobile device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random-access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the mobile device includes a display to send visual information to a user. In further embodiments, the display is a touchscreen or multi-touch-screen display.

In some embodiments, the mobile device includes an input device to receive information from a user. In some embodiments, the input device is a touch screen or a multi-touch screen.

In some embodiments, disclosed herein includes a mobile application provided to a mobile device. In some embodiments, the mobile application is provided to a mobile device at the time it is manufactured. In other embodiments, the mobile application is provided to a mobile device via a computer network, e.g., the Internet.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, and Samsung® Apps.

Communications Element

FIG. 1B show schematic diagrams of the ultrasound probe 110 and the mobile device. In this particular embodiment, the ultrasound probe and the mobile application or the mobile device is in direct communication with each other via communications elements or interfaces at the probe and the mobile device.

Disclosed herein, in some embodiments, is a communications element including a receiver, a transmitter, and/or a transceiver. In some embodiments, the receiver, the transmitter, or transceiver is configured to communicate data using one or more wireless data transfer protocols herein. For example, the receiver, the transmitter, or transceiver herein includes a radio transceiver with an antenna or connection for an external antenna for radio frequency signals. In some embodiments, the wireless data transfer protocol includes one or more of Near Field Communication (NFC), wireless USB, ultra-wide-band, ultraband, Wi-Fi, Bluetooth, Bluetooth LE, ZigBee, WiMAX, a radio-wave based protocol, a microwave-based protocol, an infrared based protocol, an optical-wave protocol, electromagnetic induction-based protocol, an ultrasonic-wave based protocol, or a sound-wave based protocol.

Single Finger Accessibility Zone

Figure 1C:
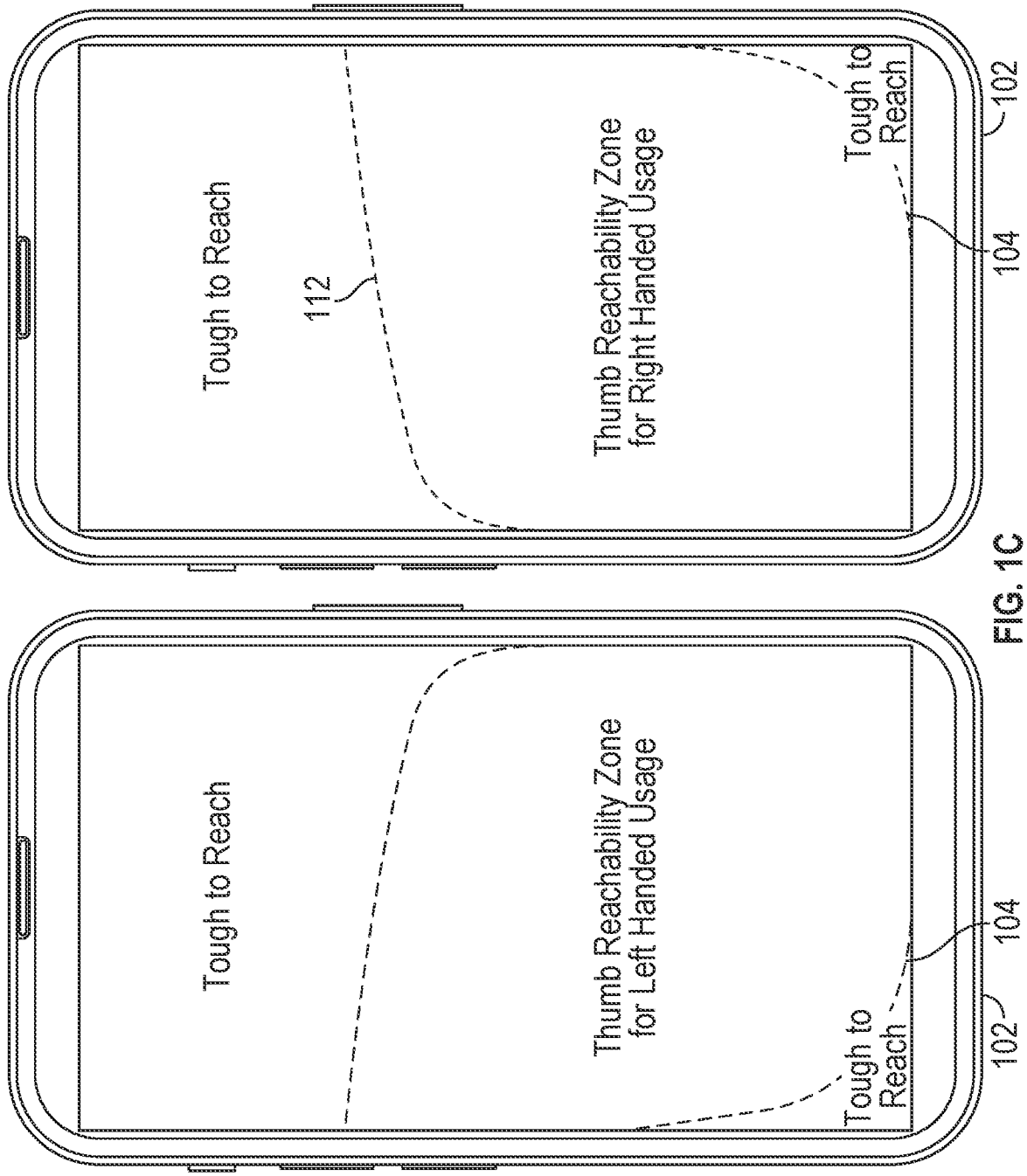
FIG. 1C shows exemplary area(s) or zone(s) on a mobile device that are suitable for thumb-based access of elements of a user interface.

Disclosed herein includes single finger accessibility areas or zones, single finger reachability areas or zones, or use of the same for left-handed user (left) and right-handed users (right) on a mobile device that are easily reachable using a single finger, e.g., a thumb, or other fingers, during single handed operation of the mobile device. The exemplary thumb reachability zone 112 is shown in FIG. 1C. In some embodiments, single finger accessibility areas or zones may be of an arbitrary shape pre-determined in the mobile application or measured for individual users during initialization of the mobile application.

In some embodiments, the size and shape of the single finger accessibility zone is determined by one or more factors including but not limited to scaled size of the user's hand, finger that operates the mobile device, the size of the mobile device, size of the input device, display size of the mobile application on the mobile device, display size of the user interface, or a combination thereof. For example, the shape and size of the single finger accessibility zone is different for a user using his thumb or index finger. Such size and shape of the single accessibility zone may be determined automatically using a process called calibration or manually determined or modified by a user to facilitate easy and more accurate operation of the mobile application. As an example, the user may customize the display size of the mobile application to be 75% of the touch screen so that is easier for her to operate the mobile application.

In some embodiments, the hand operating the mobile application is the dominant hand to allow accurate and convenient access to multiple commands and functions provided at the user interface. In some embodiments, the hand operating the mobile application is the non-dominant hand. In some embodiments, the hand operating the mobile application is also holding the mobile device. In some embodiments, the mobile device is not held by the hand interacting with the mobile application. In such cases, the mobile device may be placed or held at a support, such as a mobile phone stand or holder.

In some embodiments, the single finger accessibility zone includes one or more commonly used commands or functions therewithin for controlling operations of the portable ultrasound probe to optimize usability of the mobile application. In some embodiments, one or more non-commonly used commands or functions are positioned outside of the single finger accessibility zone.

User Interface

In some embodiments, the mobile application herein includes one or more user interfaces that allow a user to access commands and functions that controls the operation of the portable ultrasound probe.

In some embodiments, the user interface includes one or more application programmable interfaces (APIs). In some embodiments, the user interface includes one or more graphical user interfaces (GUIs). In some embodiments, the user interface includes one or more graphical icons, symbols, images, or text. In some embodiments, the user interface includes access to control various operations of the portable probe.

In some embodiments, the commonly used operational features, functions, or commands are positioned in the thumb reachability zone of a user interface. Non-limiting examples of such features include: (i) accessing presets (ii) taking images and scans (iii) changing imaging modes (iv) changing zoom settings (iv) changing brightness/contrast/pressure levels (v) adjusting time gain controls (equalizer settings) (vi) accessing and dismissing overlay functions such as pulse wave or tissue Doppler are located in the thumb reachability zone. In some embodiments, secondary operational elements that are not used regularly by a user are relegated outside the thumb usability zone. In some embodiments, one or more operational features can be moved into or outside of the thumb usability zone. In some embodiments, such movement/edit of features can be customized by a user. In addition, the thumb reachability zone can be scaled based on the size of the user's hand and mobile device being used.

In some embodiments, such operational features, commands, or functions include access to control probe operations or control a function of the mobile application. Such access can include text, symbols, icons, or a combination thereof displayed within or outside of the image display region as shown in FIGS. 2, 3A, 3B, 4A, 4B, 5, 6, 7, 8A, 8B, 8C, 9A, and 9B. For example, when an access to magnification is activated by a tap at the user interface, a magnification pad is presented to a user for adjusting image presentation parameters at the mobile application so that images are shown at a selected magnification.

In some embodiments, user interaction, e.g., actions and gestures, with the user interface via an input device in order to activate one or more functions, commands, or operational features as disclosed herein as shown in FIGS. 2, 3A, 3B, 4A, 4B, 5, 6, 7, 8A, 8B, 8C, 9A, and 9B. Non-limiting examples of such user interaction with the user interface include: a swipe, a tap, a press, a press and hold, a drag, a scrub, a scroll, a pinch, a zoom, a circling, a contouring, a crossing, their combinations, or other commonly used actions and gestures. In some embodiments, user interactions with the input device of the mobile device are converted into commands that can be transmitted via a communications element of the mobile device to the ultrasound probe, or received at the mobile application with the option to be further transmitted to the probe. In some embodiments, the user interaction is at a specified icon, symbol, and region at the interface in order to properly trigger the one or more one or more functions, commands, or operational features herein. In some embodiments, the user interaction is of one or more specified actions at the user interface.

In some embodiments, the user interaction can be customized, edited by the user to be one or more user-selected actions at one or more user-specified icons, symbols, regions, or positions of the user interface in order to activate the functions, commands, or operational features herein.

In some embodiments, commands received by the ultrasound probe via a communications element can be converted by the probe control electronics within the ultrasound device to change various settings of the ultrasound device. Non-limiting examples of such settings include imaging mode, data output settings (e.g., data format, data quality, etc.) from the ultrasound device, ultrasound frequency of operation, intensity of ultrasound pressure generated, focal depth, field of view, time gain control settings, transmit beam characteristics, receive beam characteristics, former settings, other ultrasound settings, IMU settings, and ultrasound sensor settings.

Figure 2:
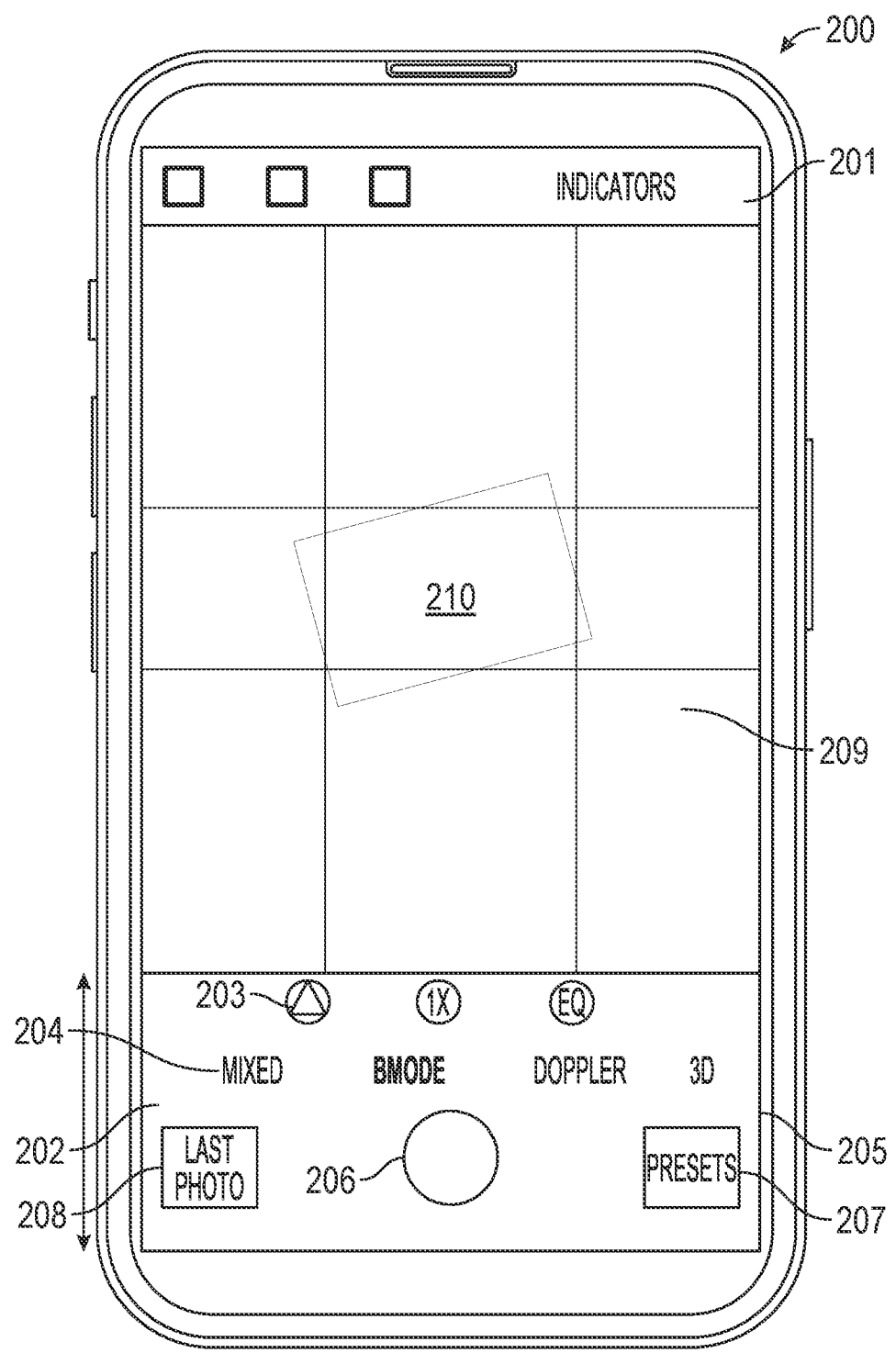
FIG. 2 shows an exemplary overview of the user interface disclosed herein.

FIG. 2 shows an exemplary layout of the user interface 200 of the mobile application disclosed herein, where the mobile application is installed on the mobile device 102. In this particular embodiment, the user interface includes a top bar 201, which is outside the thumb reachable region as shown in FIG. 1C, thus not commonly used commands and access indicators can be customized to be positioned in the top bar. Non-limiting examples of such not frequently used commands and indicators include the mechanical index and frequency of operation. In the same embodiment, a control region 202 includes a toolbar 203 for commonly used functions, a mode selector 204 for switching between different modes, e.g., B-Mode, Doppler, three-dimensional (3D) ultrasound, and mixed modes of imaging. In some embodiments, the user can swipe left or right (e.g., anywhere or close to the mode selector of the user interface) on the screen to switch between different imaging modes. In alternative embodiments, the user can tap on the name of the mode on the mode selector to switch between imaging modes. In the same embodiment, the control region includes a bottom bar 205 which includes a button for acquiring images/videos 206, selecting presets 207, viewing previous photos or videos 208, and accessing a secondary application for post processing and annotating images. In the same embodiment, the control region includes a region 209 for displaying the image/video feed from the ultrasound probe and an indicator 210 for rotation, attitude, or position of the ultrasound probe head. In some embodiments, this region can also be used to overlay instructions for the user on how to move the ultrasound probe. In some embodiments, a number of overlays which can be triggered in response to user actions are used to directly interact with the ultrasound device.

In some embodiments, the user interface herein includes a top bar which is outside of the single finger accessibility zone. In some embodiments, the single finger accessibility zone comprises at least a part of an image display region and at least a part of a control region as shown in FIG. 2.

In some embodiments, the mobile application includes one or more presets of parameters for imaging specific tissue types of a patient. For example, different presets may exist for imaging a fetal baby, a kidney, an appendix, a heart or other tissue of a patient.

Figure 3A:
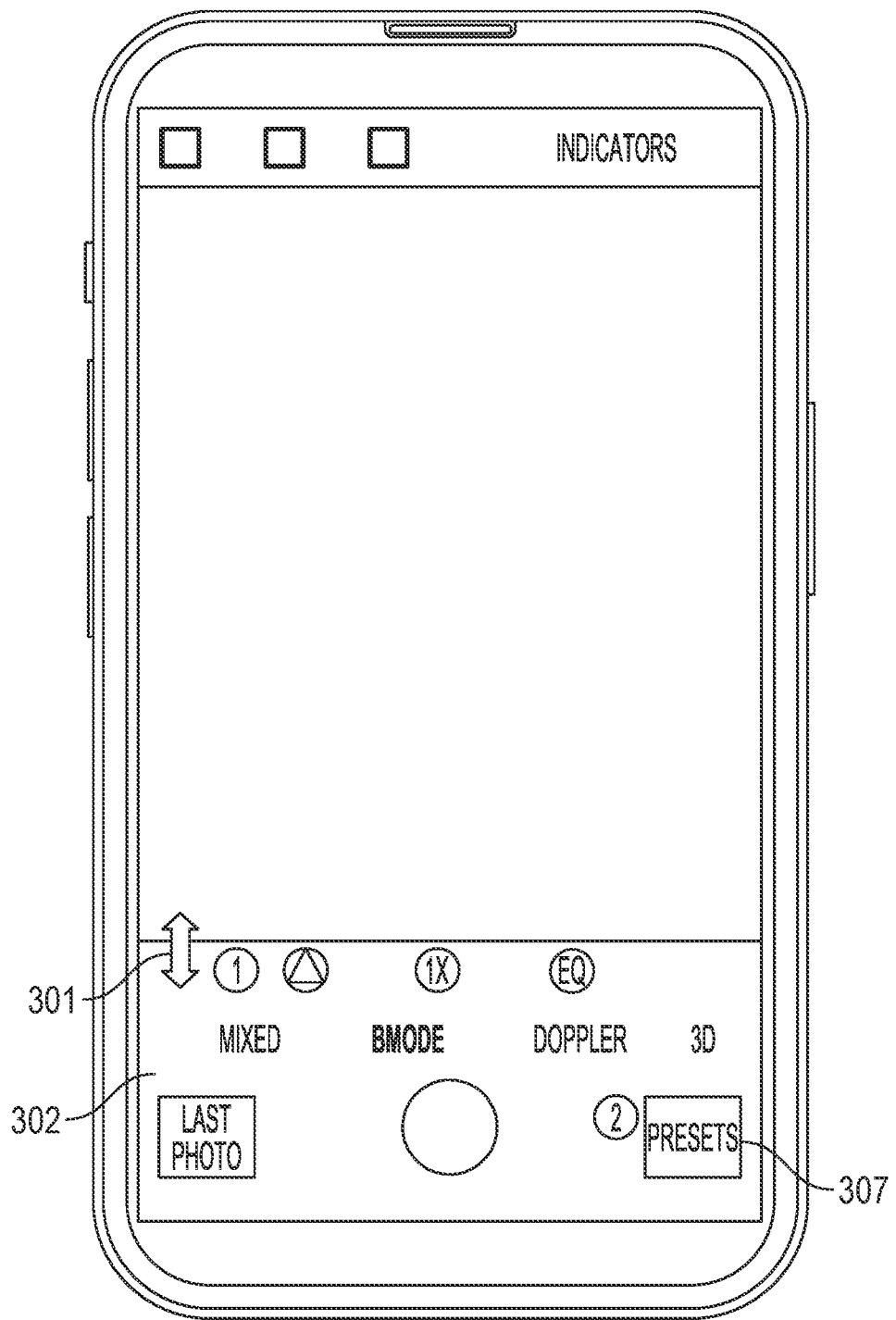
FIGS. 3A and 3B show an exemplary embodiment of the user interface for choosing preset(s) of imaging parameters.
Figure 3B:
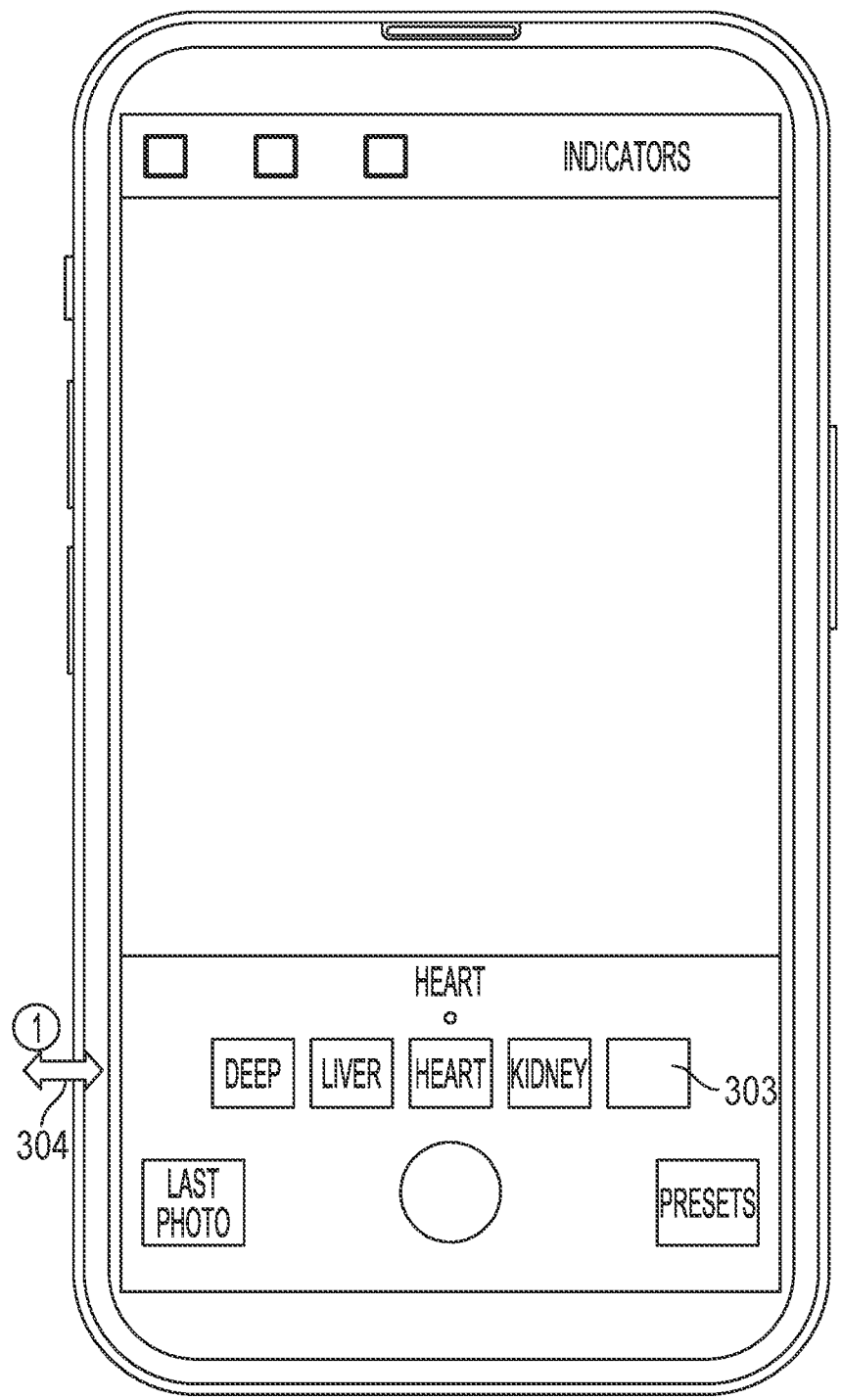

FIGS. 3A and 3B show the user interface of the mobile application which allows a user to switch between different presets of operation. In this exemplary embodiment, the user can interact with the touch screen, for example, swipe up or down 301 anywhere on the control region 302 or select the "presets" button 307 to reveal the presets pad 303, or equivalently herein, presets overlay. The user can then swipe or scrub left or right 304 on the presets bar to select the preset of interest. The presets bar can be dismissed by swiping up or down 301, for example, on the control panel. In some cases, the present bar can automatically disappear after determined time duration, for example, for about 5, 4, 3, 2 seconds or any other durations. Referring to FIG. 3A, in a particular embodiment, a user optionally (1) swipes up or (2) taps presets button to reveal a presets bar and the user optionally swipes down or taps the presets button a second time to dismiss the presets bar. Referring to FIG. 3B, in a particular embodiment, (1) presets are optionally scrolled left/right with the user's thumb to select preset(s).

Figure 4A:
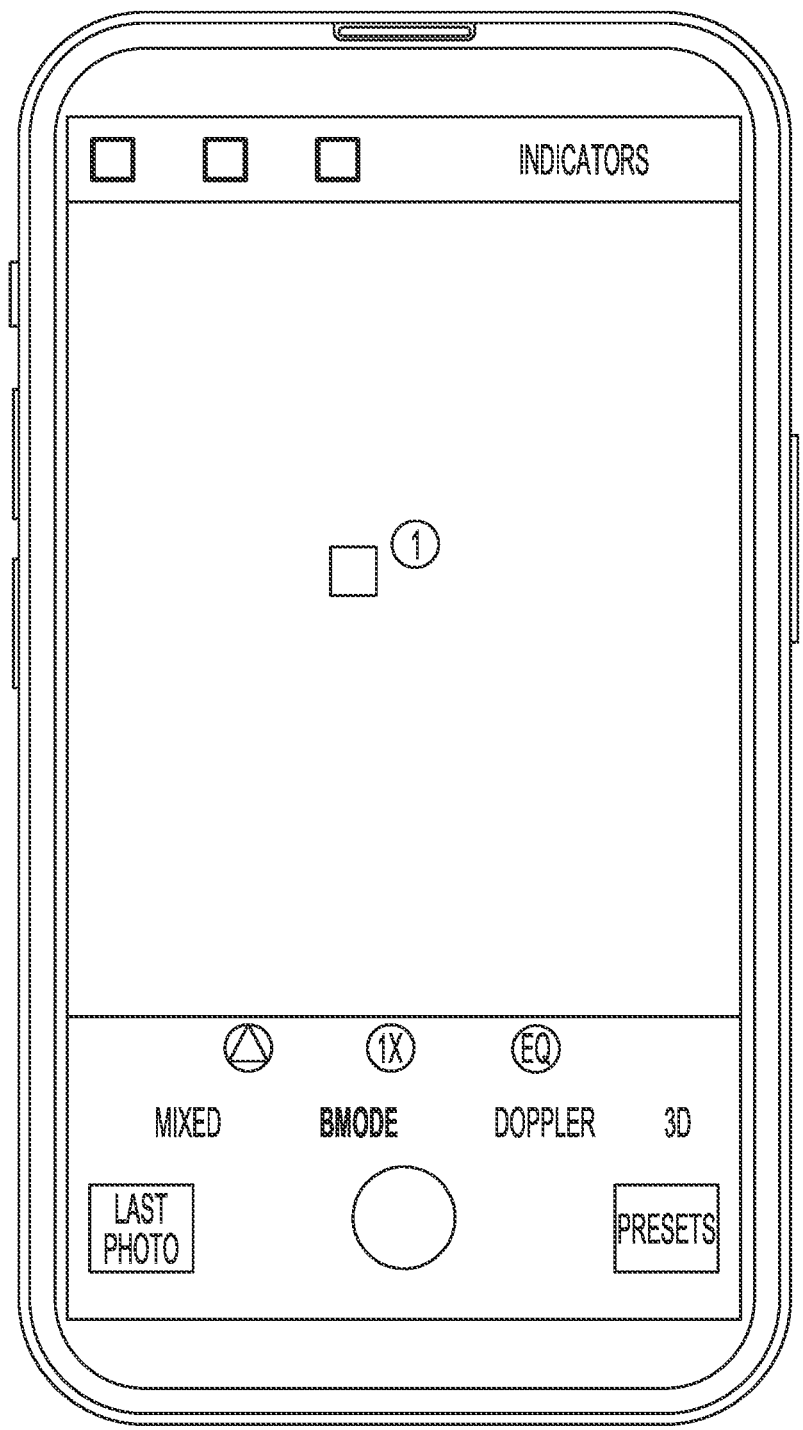
FIGS. 4A and 4B show exemplary embodiments of the user interface for setting the focal point for ultrasound image(s) (FIG. 4A) and adjusting the pressure levels of ultrasound signals (FIG. 4B)

FIG. 4A shows the user interface of the mobile application which allows the user to set the depth or focus (also known as "focus" or focal point) on the image. In this particular embodiment, the user simply taps anywhere on the image in the display region 209 in FIG. 2 to set the focal point.

Figure 4B:
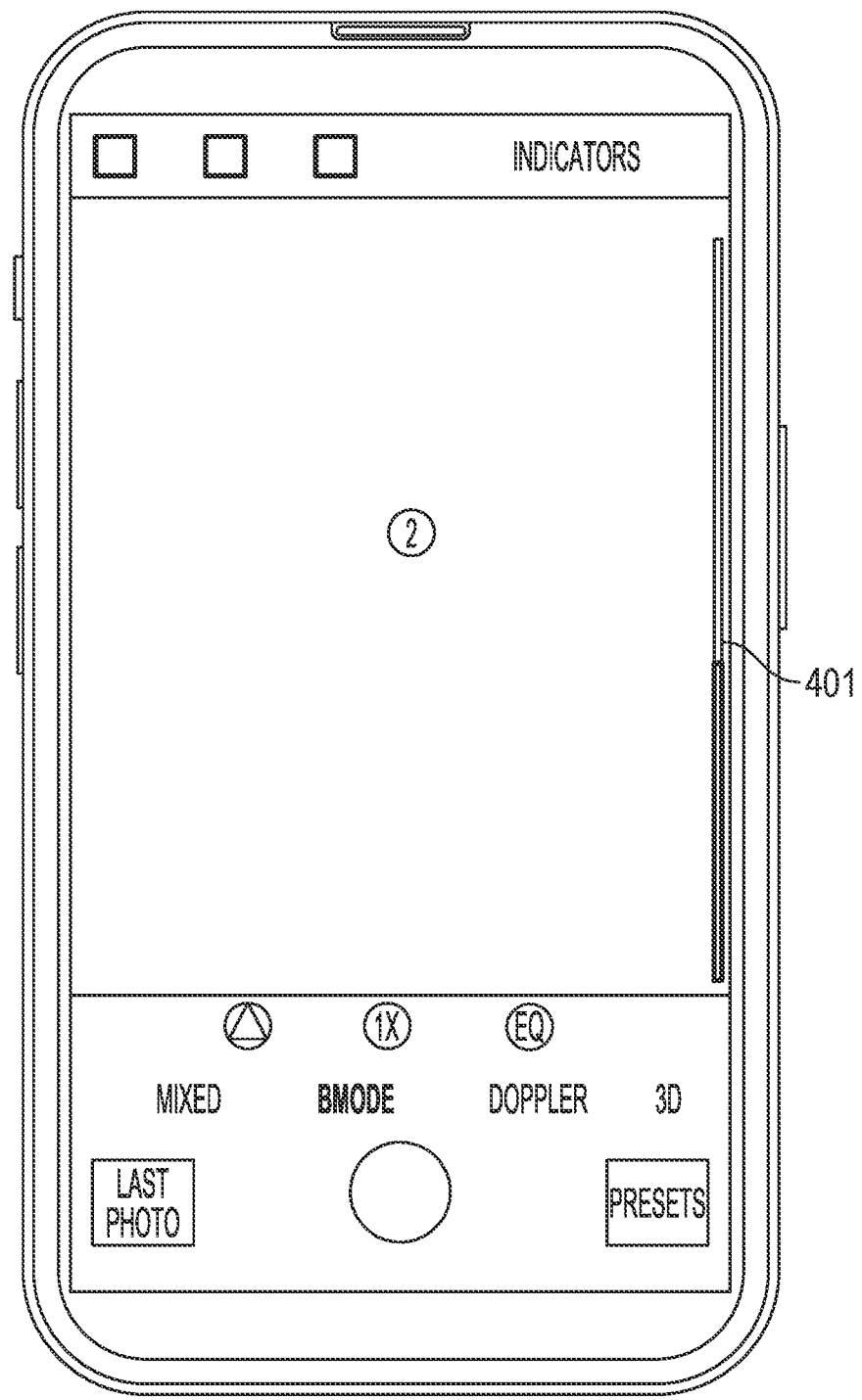

FIG. 4B shows the user interface of the mobile application which enables the user to adjust the pressure generated by the ultrasound imager. The pressure adjustment is triggered by a specified user interaction with the touch screen, for example, swiping or scrubbing up and down on the image in the display region 209 in FIG. 2. An overlay indicating the pressure level 401 can be shown on the screen. In some embodiments, the maximal and minimal pressure may be predetermined by the mobile application or customized by the user. The overlay automatically disappears after a preset time. In alternative embodiments, swiping or scrubbing up and down on the image can be customized to adjusting the overall brightness or contrast of the image.

Figure 5:
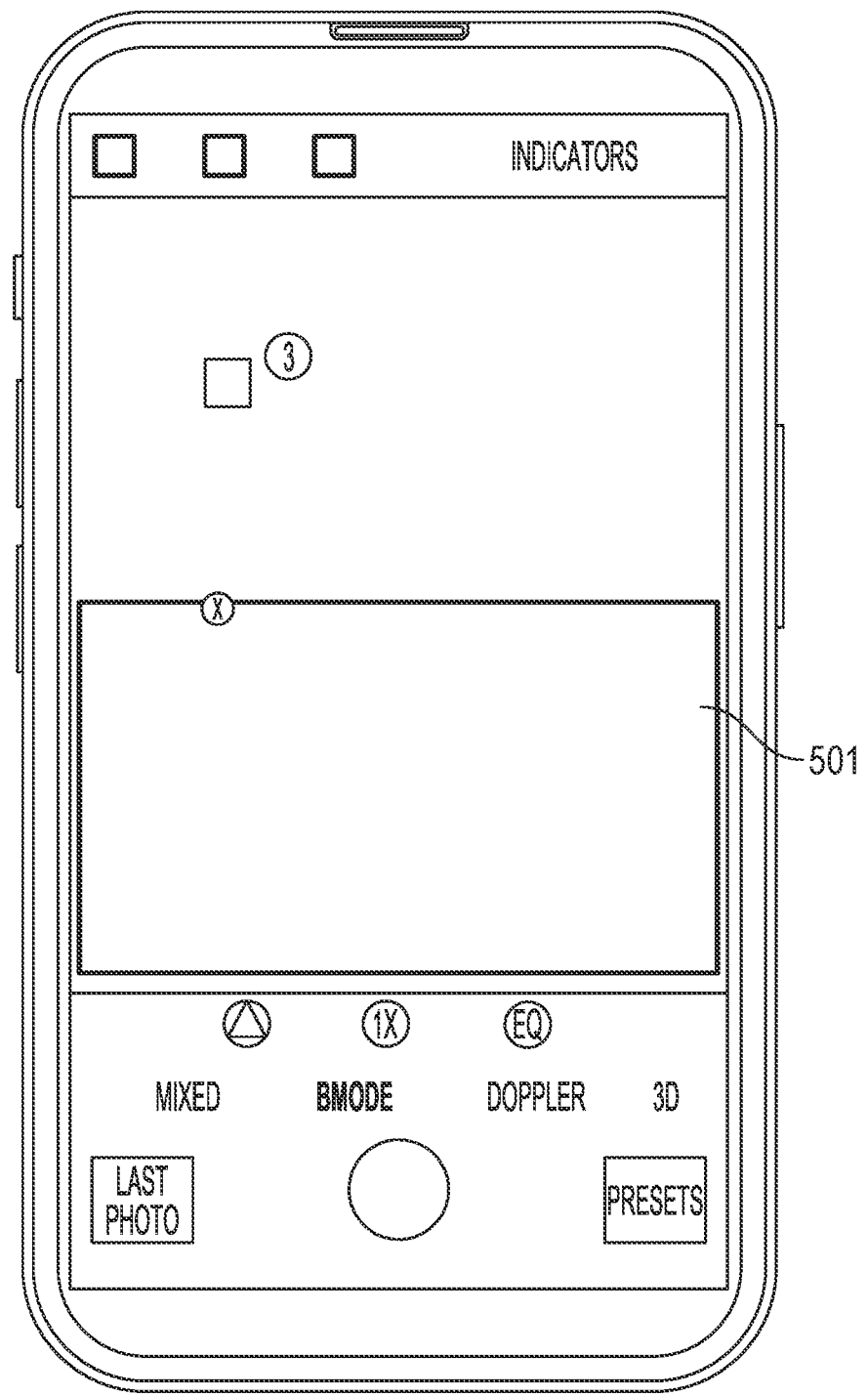
FIG. 5 shows an exemplary embodiment of the user interface for activating Doppler overlay to displayed image(s)

FIG. 5 shows the user interface of the mobile application which allows the user to observe the Doppler signal of a region of interest (e.g., pulse wave Doppler (PWD) or tissue Doppler mode). In some embodiments, PWD/tissue mode can be triggered by a specified user interaction with the touch screen, for example, a long press and hold in the region of interest of an image. This triggers a PWD/tissue mode overlay which displays the Doppler signal in the region of interest over time. The PWD/tissue mode overlay 501 can be moved up or down on the screen by dragging the overlay. The overlay can be dismissed by pressing the (x) button or simply flicking the overlay off the screen. Additional controls maybe used or added to switch between PWD and tissue Doppler modes. Referring to FIG. 5, in a particular embodiment, (3) a long tap on the image triggers a PWD overlay on the image. The motion of the selected region over time is displayed in the PWD mode overlay. Additional controls are optionally displayed on the overlay to toggle between PWD and tissue Doppler. The overlay is optionally dismissed by swiping the region up or down or tapping the (x) button.

Figure 6:
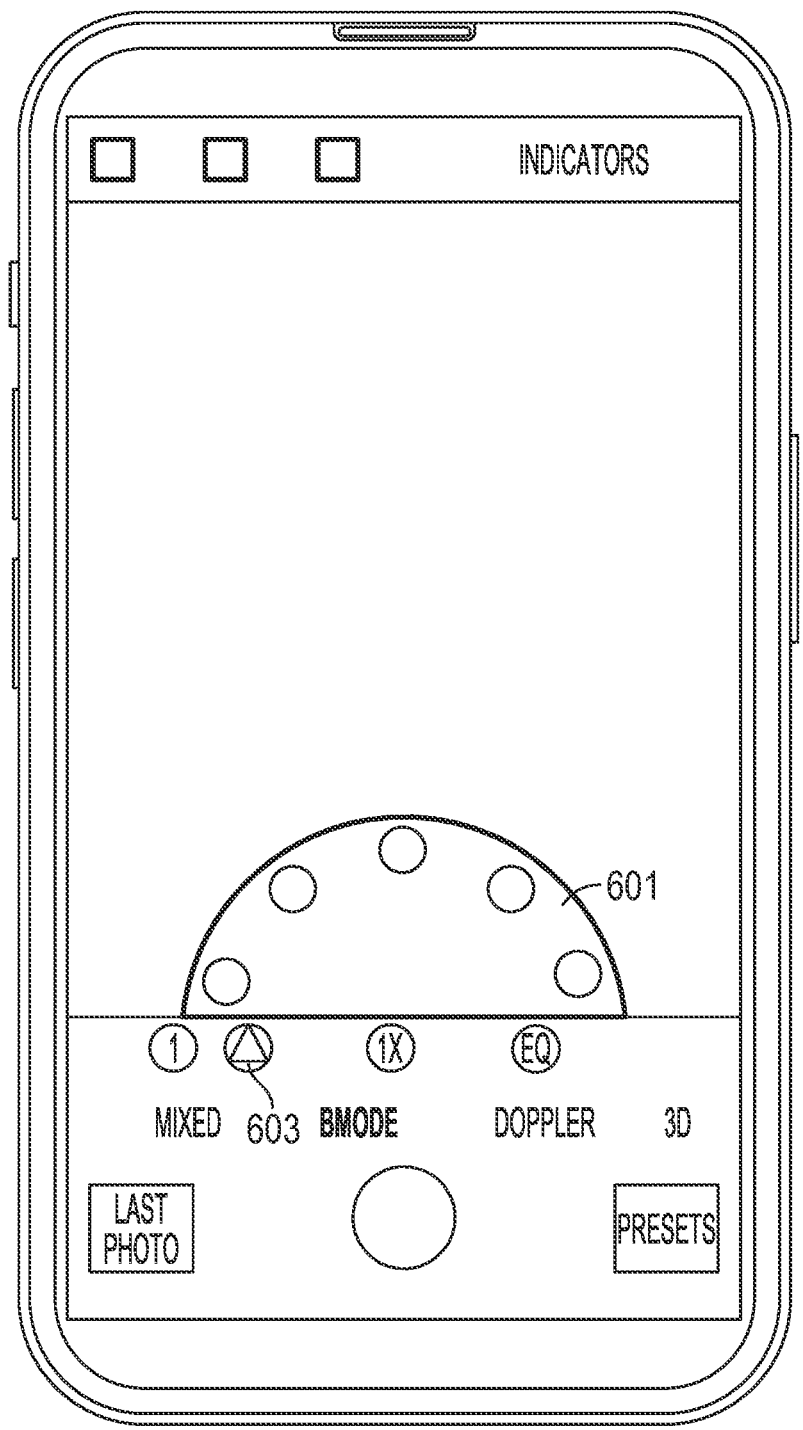
FIG. 6 shows an exemplary embodiment of the user interface for accessing controls commands and settings.

FIG. 6 shows a toolbar at the user interface which enables the user to access commonly used control commands or imaging modes using a thumb. The toolbar includes a toolbar palette 601 that can be activated or displaced by pressing the toolbar icon 603. In some embodiments, the toolbar palette includes a layout that can be accessed conveniently using the thumb or other finger. In this particular embodiment, the toolbar palette is a semicircular shape. Selecting an icon in the toolbar palette via user interaction with the icon can trigger a further action. The icons in the palette can be automatically set by the mobile application. Alternatively, the user may customize section of icons in the palette. Referring to FIG. 6, in a particular embodiment, (1) a user optionally taps on toolbar icon to reveal icons for commonly use commands and/or modes. The user optionally dismisses the toolbar region by flicking their thumb down on the region. Alternatively, the toolbar will disappear after, for example, about 5 second of inactivity.

Figure 7:
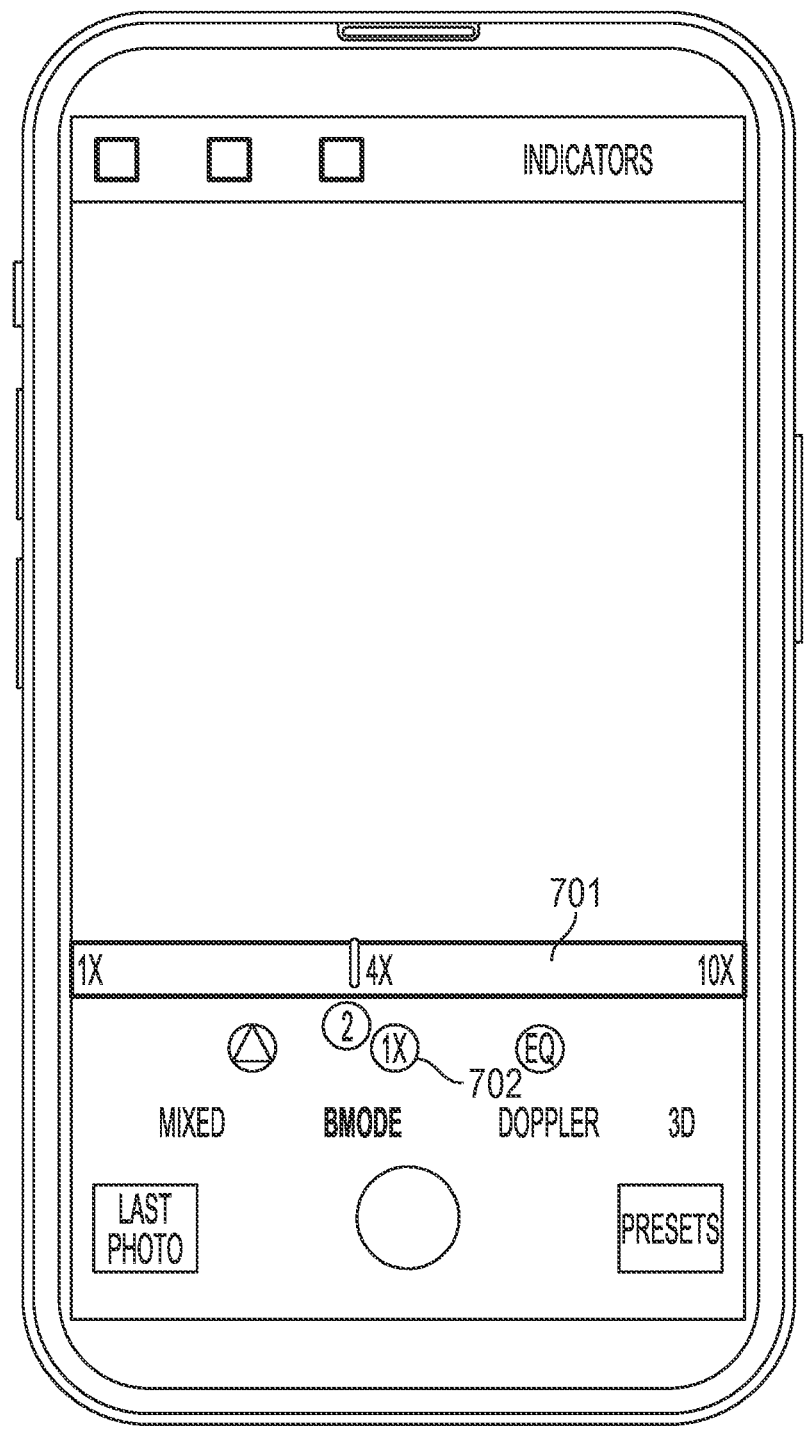
FIG. 7 shows an exemplary embodiment of the user interface for adjusting magnification of a displayed image.

FIG. 7 shows a bar at the user interface which enables the user to adjust the magnification of the image using a thumb. In this particular embodiment, when the user taps on the magnification button 702, a magnification pad 701 is presented to the user. The user can change the magnification by preselected user interaction with the magnification pad, for example, by scrubbing the magnification pad left or right until the correct magnification setting is achieved. In this embodiment, the magnification settings are applied around the depth of focus chosen by the user. Referring to FIG. 7, in a particular embodiment, (2) a user optionally taps on zoom icon to change the magnification and/or zoom in or out of the image. The user optionally scrubs the magnification pad with their thumb to select magnification of interest. The user optionally dismisses the magnification pad by flicking their thumb down on the pad. Alternatively, the magnification pad will disappear after, for example, about 5 seconds of inactivity.

Figure 8A:
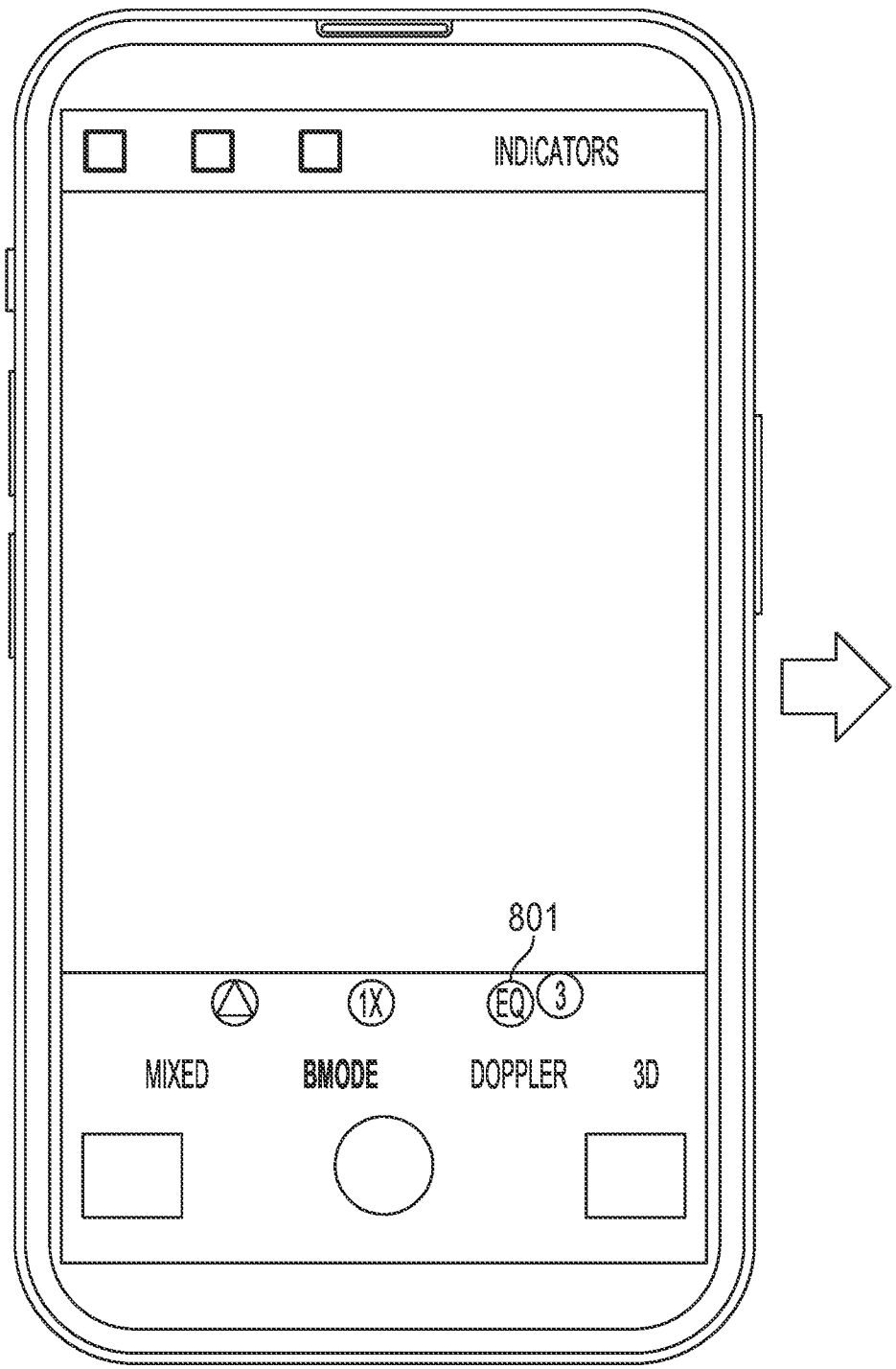
FIGS. 8A-8C show an exemplary embodiment of the user interface for adjusting time gain control settings.
Figure 8B:
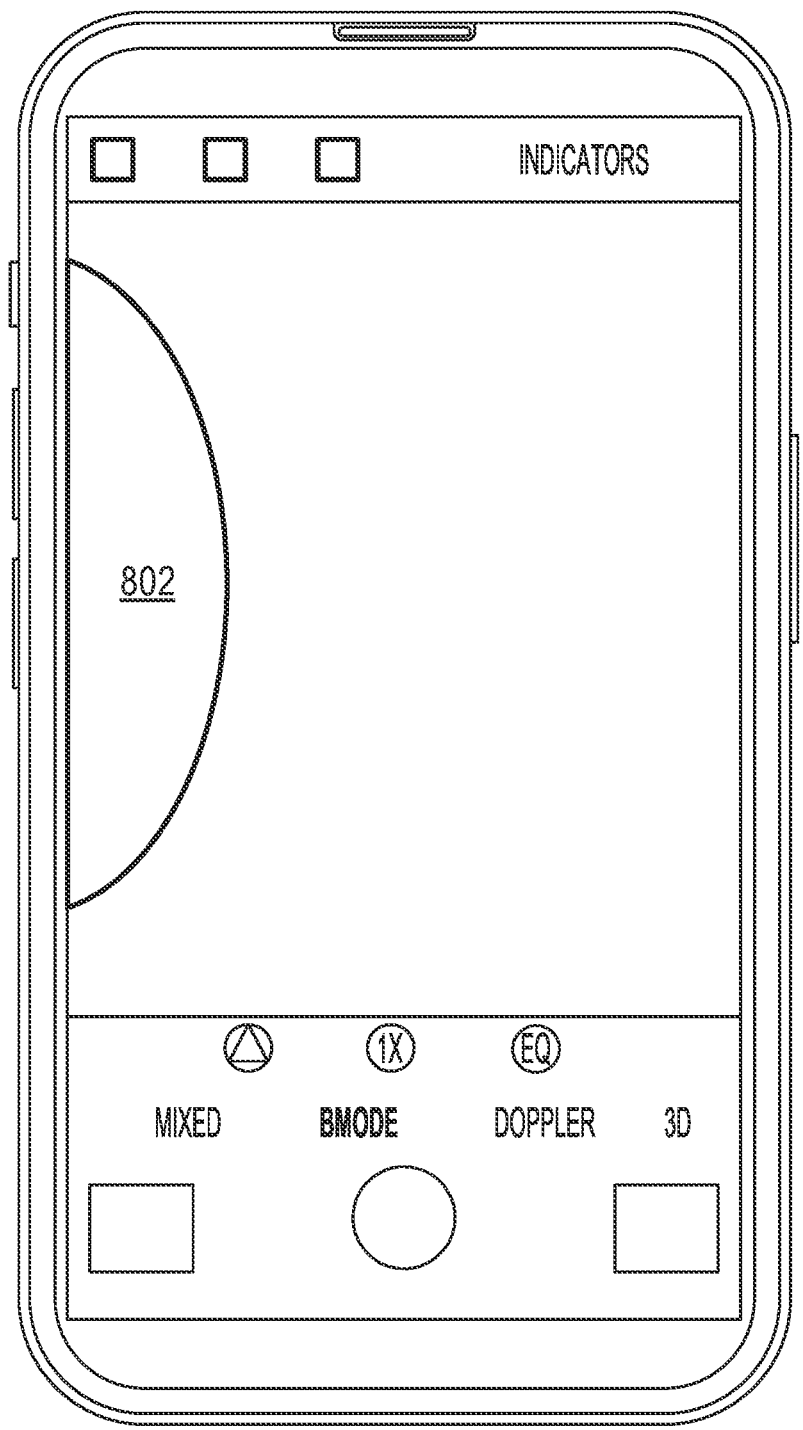
Figure 8C:
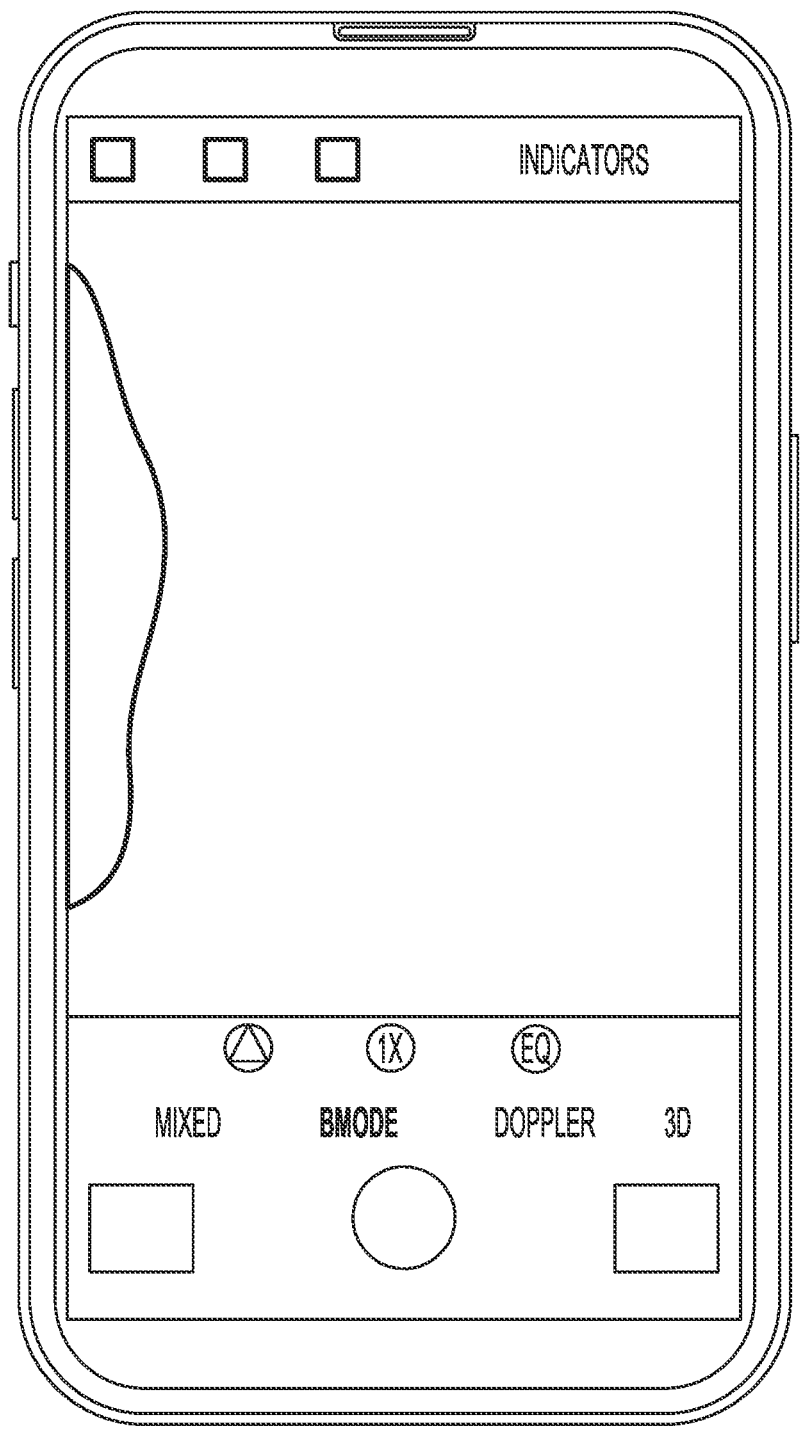

FIGS. 8A-8C show a button at the user interface which allows a user to adjust the time gain control settings, or equivalently, equalizer settings using a thumb. In this particular embodiment, when the user taps on the "EQ" button 801, an equalization overlay 802 (equivalently, as equalizer or EQ pad) is displayed on a side of the screen in the image display region. The EQ pad can be deformed by the user by moving their thumb or other digit across the pad to deform the shape of the equalizer pad, thus changing the equalization settings. The equalization settings are then translated into time gain control signals and sent back to the device. While the position of the EQ pad, in this embodiment, is shown to the left of the screen in the interface it can be customized to appear on the right-hand side of the screen for right handed operation, in other embodiments. The EQ pad can be dismissed by flicking it off the screen. The EQ pad can also disappear automatically after a preset time.

Figure 9A:
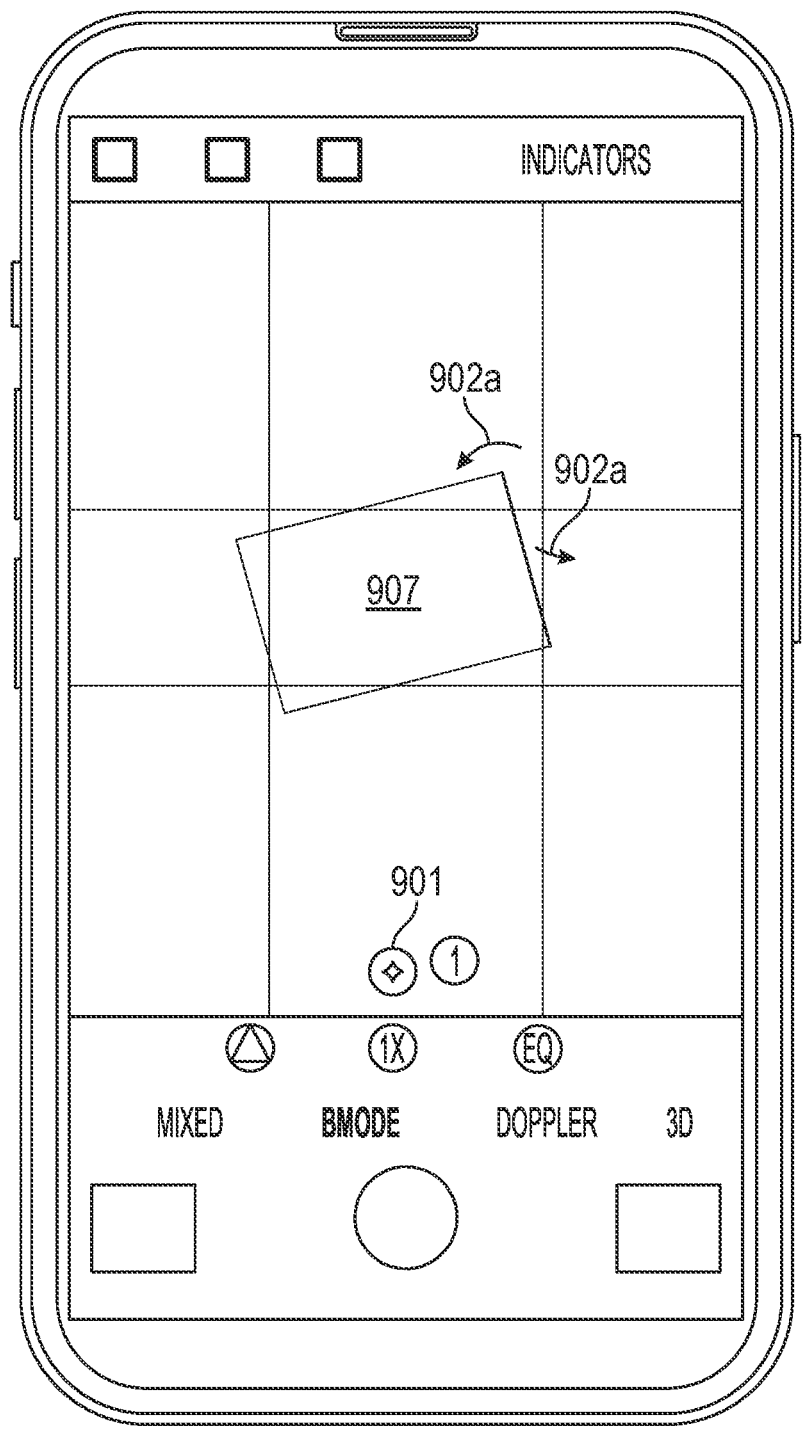
FIGS. 9A and 9B show an exemplary embodiment of the user interface for displaying guidance instructions for moving the ultrasound probe.
Figure 9B:
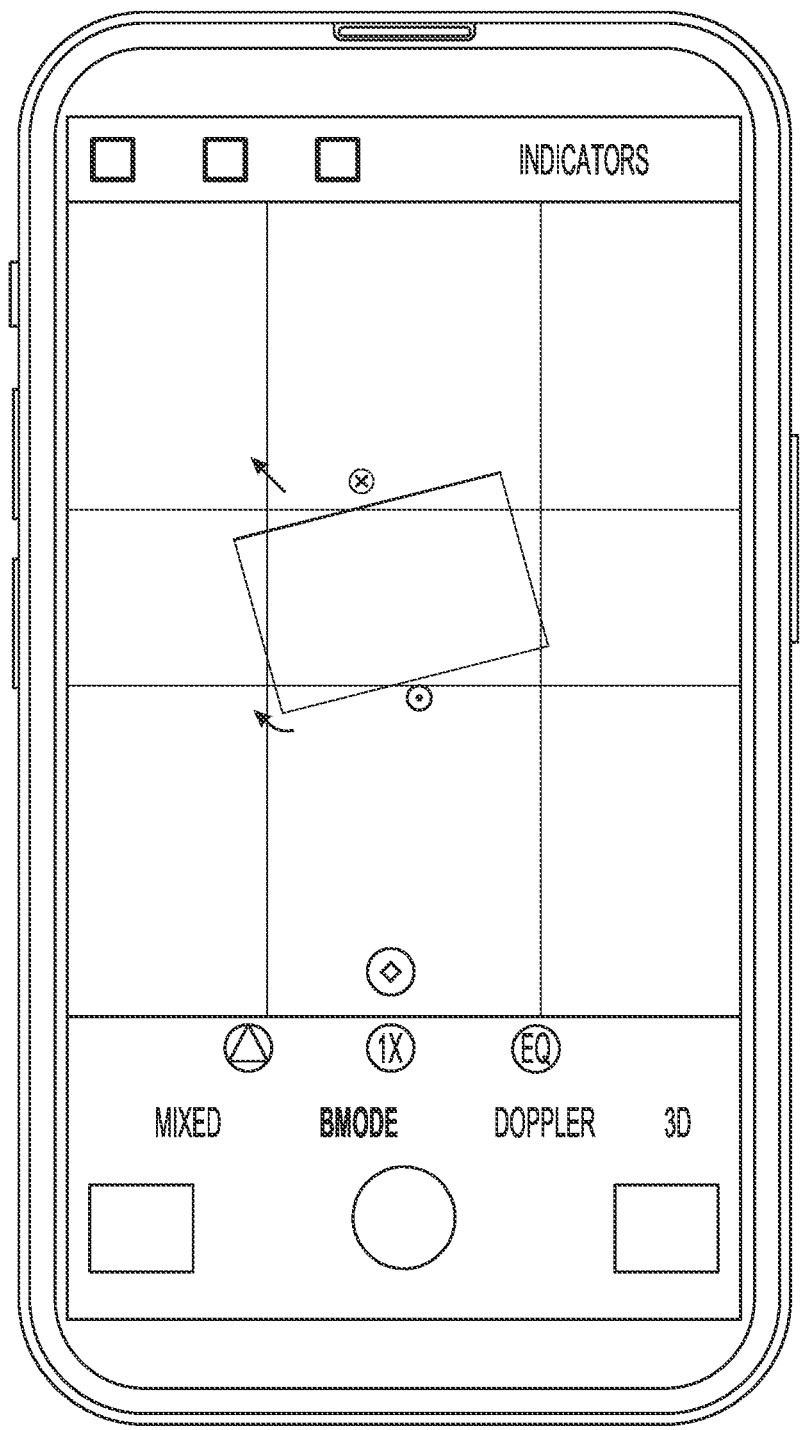

FIGS. 9A and 9B show a user interface that allows display of the orientation or attitude of the ultrasound probe and user guidance instructions as an overlay on the image. Such features of the user interface herein advantageously enable novice users to use ultrasound imaging systems herein and find clinically valid views of organs/tissue. In this embodiment, the position indicator of the probe 907 is presented as an overlay on the displayed image and changes in real-time as the user moves the probe. When guidance instructions are available for a particular procedure, a guidance icon 901 automatically appears on the screen. The user can toggle the guidance instructions on/off by tapping on the guidance icon. When guidance is turned on, the instructions 902a, 902b to move the probe are overlaid on top of the positional indicator 907. The instructions can be displayed as a combination of text and symbols, e.g., arrows to guide the user to position the imaging probe for acquiring a view of the image.

In some embodiments, the portable ultrasound probe and/or mobile device are configured to provide haptic feedback with regard to operating conditions. The haptic feedback provides a convenient additional way to provide information to the user without reducing screen real estate or requiring extra input from the user, or warning the user of critical information. In an exemplary embodiment, the ultrasound probe and/or mobile device will vary the intensity of the haptic feedback based on the orientation of the probe, with peak intensity indicating correct alignment.

In some embodiments, the portable ultrasound probe and/or mobile device are configured to provide audio signals regarding operating conditions. As with the haptic feedback, the audio signals provide an additional way to provide information to the user without reducing screen real estate or requiring extra input from the user, or warning the user of critical information. In an exemplary embodiment, the mobile device will provide a spoken warning regarding the probe transducer surface temperature when the surface temperature is within 1, 2, 3, 4, 5, 6, 7, 8, 9, or 10 degrees Celsius of the maximum allowable temperature. Alternatively, the ultrasonic probe and/or mobile device will provide an audio tone when on but not active.

In some embodiments, the portable ultrasound probe and/or mobile device/application are configured to provide visual signals regarding operating conditions. As with the haptic and audio feedback, the visual signals provide an additional way to provide information to the user without reducing screen real estate or requiring extra input from the user, or warning the user of critical information. In an exemplary embodiment, the portable ultrasound probe changes the color and/or intensity of a LED or other visual indicator in response to the user adjusting the probe and attaining an optimal orientation.

In some embodiments, the portable ultrasound probe and/or mobile device/application includes elements allowing a user to record voice annotation. In further embodiments, components allowing a user to record voice annotation comprise a microphone. In still further embodiments, a microphone is coupled with a user interface element for activating/deactivating the microphone and/or recording features. In other embodiments, a microphone is always active and listens for a trigger to start and/or stop recording features. In various embodiments, a voice annotation pertains to a patient, a procedure, an image, a region of an image, a property of an image, review of one or more images, billing issues, or attestation (e.g., digital signatures), etc.

In some embodiments, the portable ultrasound probe and/or mobile device includes elements allowing a user to select one or more texts from a list of pre-populated texts. In some embodiments, a list of pre-populated texts is presented on a display and the user selects one or more via touch, voice, or the like. In various embodiments, a user-selected text pertains to a patient, a procedure, an image, a region of an image, a property of an image, review of one or more images, billing issues, or attestation (e.g., digital signatures), etc.

What is claimed is:

1. A portable ultrasound imaging system comprising:
a portable ultrasound probe configured to be operable using a first hand; and
a mobile application having instructions configured to be executed by a processor on a mobile device and to cause the mobile device to display a user interface that:
(i) is operable using a second hand while a user simultaneously operates the portable ultrasound probe with the first hand;
(ii) comprises a single-finger accessibility zone configured to be reachable using a single finger during single-handed use of the mobile device,
the single-finger accessibility zone having a size and shape that is measured for individual users during a calibration process that occurs during initialization of the mobile application,
the single-finger accessibility zone encompassing a majority of the user interface and including an image display region and a control region; and
wherein the portable ultrasound probe is configured to connect to the mobile device to allow a user to control an operation of the portable ultrasound probe the single finger accessibility zone for imaging via user interaction with the user interface.

2. The system of claim 1, wherein the size and shape of the single-finger accessibility zone is configured to be determined during a calibration process or manually determined by the user.

3. The system of claim 1, wherein the single-finger accessibility zone is configured to be different for the individual users when using different fingers.

4. The system of claim 1, wherein the instructions cause the user interface to provide access to commonly used commands or functions within the single-finger accessibility zone.

5. The system of claim 1, wherein the single-finger accessibility zone is scaled based on size of the second hand, size of the mobile device, size of a touch screen of the mobile device, display size of the mobile application, display size of the user interface, or a combination thereof.

6. The system of claim 1, wherein the portable ultrasound probe is configured to connect with the mobile device via a direct electronic communication configured to allow a user to control an operation of the portable ultrasound probe for imaging via user interaction with the user interface.

7. The system of claim 6, wherein the direct electronic communication between the portable ultrasound probe and the mobile device is wired or wireless.

8. The system of claim 1, wherein a size and a shape of the single-finger accessibility zone can be modified by the user.

9. The system of claim 1, wherein the user interface is configured to be operable using only one finger of the second hand of the user.

10. The system of claim 1, wherein the second hand of the user is a dominant hand or a non-dominant hand of the user.

11. The system of claim 1, wherein the mobile device comprises a touch screen configured to allow user interaction with the user interface of the mobile application.

12. The system of claim 11, wherein the user interaction with the user interface via the touch screen comprises: a swipe, a tap, a press, a press and hold, a drag, a scrub, a scroll, a pinch, a zoom, a circling, a contouring, a crossing, or a combination thereof.

13. The system of claim 1, wherein the user interface provides access to one or more non-commonly used commands or functions outside of the single-finger accessibility zone.

14. The system of claim 1, wherein providing access to commonly used commands or functions within the single-finger accessibility zone comprises displaying text, symbols, or icons.

15. The system of claim 14, wherein the text, symbols, or icons are at least partly overlaid with an image after the user activates the text, the symbols, or the icons.

16. The system of claim 1, wherein the control region comprises an imaging toolbar, an imaging mode selector, an imaging preset button, or an access to image processing.

17. The system of claim 1, wherein the portable ultrasound probe comprises a communication interface that is configured to allow direct electronic communication between the portable ultrasound probe and the mobile device.

18. The system of claim 17, wherein the mobile device comprises a second communication interface that is configured to allow the direct electronic communication between the portable ultrasound probe and the mobile device.

19. The system of claim 17, wherein the direct electronic communication between the portable ultrasound probe and the mobile device is wired or wireless.

20. The system of claim 1, wherein the portable ultrasound probe comprises an ultrasound transducer, an inertial measurement unit (IMU) sensor, a pressure sensor, a force sensor, a unit for probe control, or a combination thereof.

21. The system of claim 1, wherein the portable ultrasound probe, the mobile device, or both are configured to provide a user interface allowing a user to select one or more texts from a list of pre-populated texts.

* * * * *